Aug. 27, 1935. R. G. HASS Plant Pat. 139
AVOCADO
Filed April 17, 1935
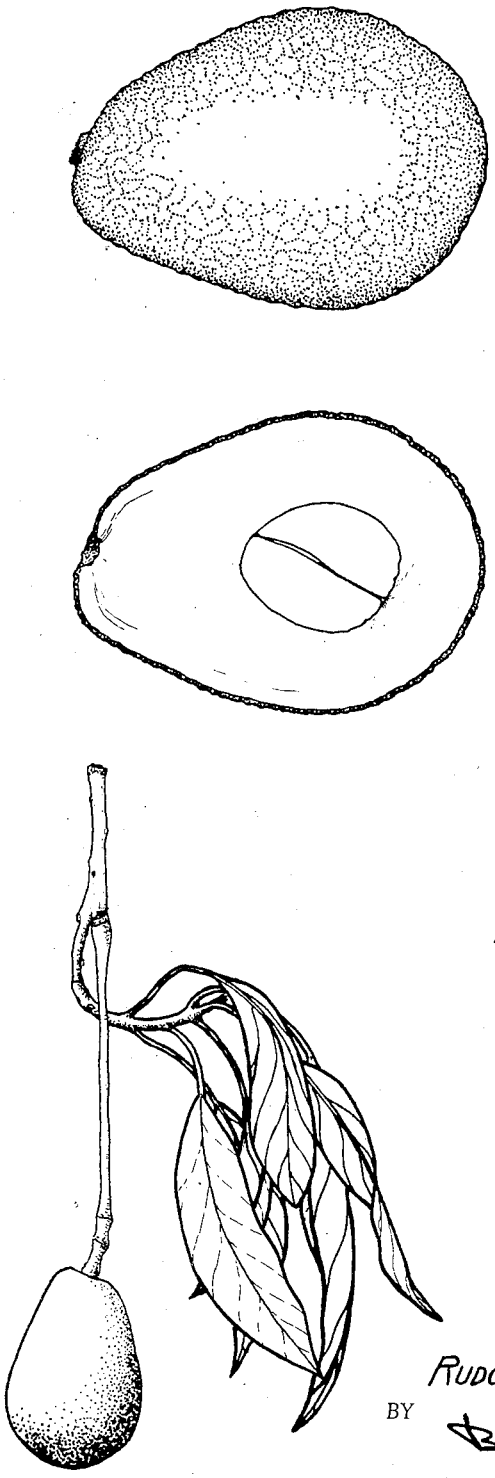
INVENTOR.
RUDOLPH G. HASS
BY B. J. Craig,
ATTORNEY.

Patented Aug. 27, 1935

Plant Pat. 139

UNITED STATES PATENT OFFICE

139

AVOCADO

Rudolph G. Hass, La Habra Heights, Calif.

Application April 17, 1935, Serial No. 16,837

1 Claim. (Cl. 47—62)

This invention relates to a new and improved variety of avocado which has certain characteristics which are highly desirable.

The original tree is a Guatemalian seedling of unknown parentage. It was planted in the spring of 1926, in a grove on West Road in La Habra Heights, Los Angeles County, State of California.

The tree has a medium, upright habit of growth, about thirty feet tall, and is quite uniform in general appearance.

The new variety has been successfully propagated on thin skinned Mexican seedlings as root stock.

This avocado is characterized by the rapidity of growth of budded stock. Two year old buds have attained a diameter of somewhat over three inches. The young branches of the tree have substantially the same color as that of the Fuerte.

The foliage is distinct. The mature leaves are green and are waved or rippled along the edges, some fully developed leaves having a length of fourteen inches or more and a width of about four inches. The newly formed leaves are about the same width as those of the Fuerte. The principal leaf veins are pronounced while the minor veins are not distinct and the leaf as a whole is quite smooth and not puckered. The mature leaves are longer and darker green than the Pueblo. The upper surface of the leaves is smooth and somewhat glossy. The lower surface is dull with a grayish cast.

The present avocado blossoms in the spring. The bloom grows in small bunches evenly distributed and the leaf drop during the blooming season is slight.

The trees of this invention bear the second or third year. The fruit is pyriform in shape and is borne on long light greenish-yellow stems with the stems of larger diameter than those on the Fuerte. The stems vary in length from four to thirteen inches, a fair average being six inches.

The button is normal and the line of division between the button and stem is not particularly noticeable nor is the button cavity, which is usually disposed slightly at one side of the longitudinal axis of the fruit, large. The attachment of the button to the stem and of the stem to the tree is strong so that relatively high winds are not destructive to the fruit.

The fruit crop is consistently heavy and is evenly distributed about the tree. The fruit matures during the summer: namely, from May to September. There is no tendency to overbearing and consequent stunting of the tree. The fruit when green somewhat resembles the Fuerte in exterior appearance but is much rougher. The fruits average from six to ten ounces when mature, although in young trees the average weight is slightly higher. The color of the fruit is common to that of the Guatemalians, being dark, glossy green when mature on the tree. The skin of the picked fruit gradually turns to a mixed purple and green and then dark purple as it approaches the edible stage and remains slightly pebbled.

The fruit hangs dependent, occasionally two on a stem, although usually there is only one fruit on a stem.

The general outside appearance of the fruit is quite pleasing which is usually not the case with dark fruit.

The keeping qualities of the fruit are very good and the skin of the fruit is thin for a Guatemalian and is leathery. The shipping qualities are therefore excellent. The fruit has no blemishes or defects.

The surface spots are yellow in color, with a few reddish brown. They are pin point in size and medium in number.

The flesh is a rich cream color of butter consistency with no fibre and with excellent nutty flavor. The oil content is 18.30%.

The seed is tight in the cavity; the average weight is about one ounce; the surface is smooth, the color light yellow, the texture hard. The seed coat is thin, brown and adheres tightly to the seed.

The arrangement of the seed in the fruit and its size is such that when the seed is removed the seed coat is always withdrawn with the seed, the seed cavity is symmetrically disposed so that a pleasing appearance is obtained.

The present avocado differs from the Dickinson in that the latter has a lower oil content, extremely hard shell and larger seed.

It will be understood that the characteristics of this invention will vary slightly under various conditions of climate, topography, soil, and care.

The beneficial characteristics of this tree are that it bears an excellent small summer maturing fruit, when good small fruit are scarce, the fruit having a thin, for Guatemalian, leathery skin and having a small tight seed and with flesh of excellent color and nutty flavor, smooth and butter-like and with the fruit borne on long stems.

The present avocado differs from the Cabnal in that the latter is round, rough and green, whereas the present fruit is pyriform and a dark color.

The fruit of the invention differs from the Carabas in that the latter is green and averages sixteen ounces, whereas the fruit of the present invention is purple and averages about eight ounces.

My invention has fruit differing from the Colorado in that the latter fruit weighs one pound or more and has lower oil content and poor flavor and the habits of growth are quite different from the present invention.

The fruit of the present invention differs from the Dutton and the Spinks in that there is no internal or external rotting or dropping before maturity.

The invention differs from the Mayapan in that its fruit is smoother and is of good quality and the fruit does not drop; further, the present invention bears fruit with thin skin, for Guatemalian, which is quite a contrast with the thick skin of the Mayapan.

The present invention differs from the Taft in that my tree bears earlier and bears regularly. Further, it does not scab or crack or drop.

The present invention differs from the Murrieta Green, which is a summer fruit, in that the latter is dark green and the trees are not vigorous, while the fruit of the present avocado is purple and the trees are of a vigorous healthy growth.

The present invention differs from Sharpless in that its fruit does not soften and decay on the tree.

The present invention differs from the Laurel, which also bears summer fruit, in that its fruit does not crack or split on the end and is not susceptible to blast, and is purple.

I claim as my invention:

The variety of avocado tree herein described characterized by its summer ripening, medium-sized fruits, of purple color having a leathery skin which is thin for a Guatemalian, and borne on long stemps, with a small tight seed and with creamy flesh of excellent color and nutty flavor, smooth with no fibre and butter-like consistency.

RUDOLPH G. HASS.